US007049479B2

(12) United States Patent
Cleary et al.

(10) Patent No.: US 7,049,479 B2
(45) Date of Patent: May 23, 2006

(54) ULTRA THIN FILM TRANSDERMAL/DERMAL OR TRANSMUCOSAL/MUCOSAL DELIVERY SYSTEM

(75) Inventors: Gary W. Cleary, Lost Altos Hills, CA (US); Adrian L. Faasse, Jr., Carmel Valley, CA (US)

(73) Assignee: Corium Corporation, Grand Rapids, MI (US)

( * ) Notice: Subject to any disclaimer, the term of this patent is extended or adjusted under 35 U.S.C. 154(b) by 93 days.

(21) Appl. No.: 10/625,327

(22) Filed: Jul. 23, 2003

(65) Prior Publication Data
US 2004/0138603 A1    Jul. 15, 2004

Related U.S. Application Data

(63) Continuation-in-part of application No. 10/071,713, filed on Feb. 7, 2002.

(51) Int. Cl.
*A61F 13/00*    (2006.01)

(52) U.S. Cl. .......................... 602/57; 602/52; 602/602; 602/58

(58) Field of Classification Search ............ 602/41–59; 604/304–308; 424/443–449; 206/440, 441
See application file for complete search history.

(56) References Cited

U.S. PATENT DOCUMENTS

| 4,310,509 A | * | 1/1982 | Berglund et al. ........... 424/448 |
| 4,372,303 A | | 2/1983 | Grossmann et al. |
| 4,485,809 A | | 12/1984 | Dellas |
| 4,598,004 A | | 7/1986 | Heinecke |
| 4,600,001 A | | 7/1986 | Gilman |
| 4,614,183 A | | 9/1986 | McCracken et al. |
| 4,643,180 A | * | 2/1987 | Feld et al. ................... 604/307 |
| 4,753,232 A | | 6/1988 | Ward |
| 4,816,258 A | | 3/1989 | Nedberge et al. |
| 4,875,473 A | | 10/1989 | Alvarez |
| 4,884,563 A | | 12/1989 | Sessions |
| 4,917,112 A | | 4/1990 | Kalt |
| 4,917,929 A | | 4/1990 | Heinecke |
| RE33,353 E | | 9/1990 | Heinecke |
| 4,997,655 A | | 3/1991 | Nagy et al. |
| 5,000,172 A | | 3/1991 | Ward |
| RE33,727 E | | 10/1991 | Sims |
| 5,052,381 A | * | 10/1991 | Gilbert et al. ................ 602/52 |
| 5,088,483 A | | 2/1992 | Heinecke |

(Continued)

FOREIGN PATENT DOCUMENTS

GB    2157955 A    * 11/1985

(Continued)

*Primary Examiner*—Kim M. Lewis
(74) *Attorney, Agent, or Firm*—Price, Heneveld, Cooper, DeWitt & Litton, LLP

(57) ABSTRACT

An ultra thin film transdermal, dermal, transmucosal, mucosal pharmaceutical delivery system is disclosed, which has a handle adhered by a first adhesive to an ultra thin film layer. The opposite side of the ultra thin film is coated with a second adhesive layer, and carries an active ingredient. The handle adheres firmly to the ultra thin film layer, but does not adhere to skin, mucosa, or the silicone coated surface of a release liner. A portion of the handle extends beyond an edge of the ultra thin film to facilitate separation of the film from the release liner, and handling thereof. The second adhesive is more aggressive with respect to the patient's skin than the first adhesive is with respect to the surface of the ultra thin film, whereby the handle can be peeled away from the ultra thin film after the film has been applied to the patient.

7 Claims, 3 Drawing Sheets

U.S. PATENT DOCUMENTS

| | | |
|---|---|---|
| 5,160,315 A | 11/1992 | Heinecke et al. |
| 5,336,162 A | 8/1994 | Ota et al. |
| 5,498,417 A * | 3/1996 | Lhila et al. ................. 424/448 |
| 5,520,629 A | 5/1996 | Heinecke et al. |
| 5,531,855 A | 7/1996 | Heinecke et al. |
| 5,599,289 A | 2/1997 | Castellana |
| 5,628,724 A * | 5/1997 | DeBusk et al. ............... 602/58 |
| 5,722,943 A | 3/1998 | Sessions |
| 5,738,642 A | 4/1998 | Heinecke et al. |
| 5,762,620 A * | 6/1998 | Cartmell et al. .............. 602/42 |
| 5,951,505 A | 9/1999 | Gilman et al. |
| 6,043,406 A | 3/2000 | Sessions et al. |

FOREIGN PATENT DOCUMENTS

JP      03227919 A   * 10/1991

* cited by examiner

ULTRA THIN FILM TRANSDERMAL/DERMAL OR TRANSMUCOSAL/MUCOSAL DELIVERY SYSTEM

CROSS-REFERENCE TO RELATED APPLICATION

This application is a continuation-in-part of U.S. application Ser. No. 10/071,713, filed Feb. 7, 2002 and entitled WOUND DRESSING/IV HOLD-DOWN/DRAPE AND METHOD FOR MAKING THE SAME, which is hereby incorporated herein by reference

BACKGROUND OF THE INVENTION

The present invention relates to transdermal/dermal, or transmucosal/mucosal drug delivery systems. Transdermal refers to such delivery systems delivering an active that passes through the skin and into the circulating system. Dermal refers to systems with actives delivered to the skin. In transmucosal delivery systems, the active passes through mucosal tissue. In mucosal delivery systems, the active is delivered to the mucosal tissue.

Such delivery systems typically deliver the active via a gel modulated system, membrane modulated system, or an adhesive modulated system. In a gel system the active ingredient, usually a drug, is generally combined with other non-active ingredients to form a gel or paste. This gel is then coated onto a backing member comprising a polymeric film generally on the order of 2 mils or greater in thickness. The gel directly contacts the skin and the overlying backing film includes an adhesive coated surface extending beyond the gel perimeter to hold the assembly on the skin. The membrane modulated system is similar, but has a rate controlling film or membrane over the gelled composition which controls the rate of release of the active composition into the skin.

The adhesive modulated system incorporates the active directly into an adhesive. The adhesive has the ability to control the rate of absorption of the active into the patient's skin. The adhesive mixture is applied to the polymeric backing film which is directly applied to the patient's skin, eliminating the need for the rate controlling membrane and the need for an active containing gel.

Transdermal/dermal, or transmucosal/mucosal delivery systems must reside on the patients skin or mucosa for an extended period of time in order to allow for absorption and subsequent systemic introduction of the active ingredient. However, patients' activities such as bathing and exercising can create forces which act to detach the delivery system from the patients skin or mucosa either directly or by attacking the adhesive. As the residence time of the delivery system increases, the more problematic the long term adhesion of the delivery system becomes.

Currently, there are only three transdermal products that are designed for a seven day residence time. These are Climara® (estradiol), EVRA® (contraceptive steroids), and Catapres® (Clonidine). Climara® and EVRA® both utilize an adhesive modulated system, whereas Catapres® uses the adhesive modulated system in conjunction with an adhesive overlay. The overlay is separately packaged and the patient applies the adhesive overlay only when needed. In this manner the patient can extend the residence time of the delivery system by replacing the used overlays with new ones as they wear out.

SUMMARY OF THE INVENTION

A transdermal, dermal, transmucosal, mucosal active delivery system is provided which utilizes an ultra thin polymeric film, under 0.002 inches, rather than the typical 2 mil or more polymeric film thickness that have been used in the past. These ultra thin polymeric films provide several advantages to the delivery system. These advantages include: having smaller sink conditions thereby decreasing the migration of active ingredients, solubilizers, and other soluble molecules to the backing or other layers of the delivery system; stabilization of the adhesive properties of the film layers to allow better adhesion to skin, mucosa, wound bed periphery and the various layers of the system itself; improvement of the breathability or non-occlusive properties of the system which is important in wound care, adhesion to skin and mucosa, and irritation of the biological membrane; improvement of flexibility and endurance of the delivery system during its use or application; and the noticeability and awareness of the system is reduced thereby increasing the comfort of the system.

In a preferred aspect of the present invention, the transdermal, dermal, transmucosal, mucosal delivery system includes a handling member having a first adhesive layer coated on a first side. The first adhesive layer of the handling member is adhered to the second side of an ultra thin polymeric film having a thickness under 0.002 inches with the handling member at least partially extending beyond at least one edge of the ultra thin polymeric film. The first adhesive layer used to coat the handling member has a firm but releasable adhesive affinity for the ultra thin polymeric film, but a low affinity for a release liner and skin. A second adhesive layer is coated on a first side of the ultra thin polymeric film. An active ingredient or active ingredient coating compound is incorporated into the second adhesive layer, or is otherwise secured or adhered to the first side of the ultra thin polymeric film. A release liner is adhered to the second adhesive layer of the ultra thin polymeric film, the release liner at least partially extending beyond at least one edge of the ultra thin polymeric film, such that it is also covers the first adhesive layer of the handling member.

In use, the second adhesive layer adheres more aggressively to skin or mucosa than the first adhesive layer adheres to the second side of the ultra thin polymeric film. Therefore, the handling member can be removed from the second side of the ultra thin polymeric film once the first side of the ultra thin polymeric film is adhered to a patient's skin or mucosa.

These and other features, advantages, and objects of the present invention will be further understood and appreciated by those skilled in the art by reference to the following specification, claims and appended drawings.

DESCRIPTION OF THE PREFERRED EMBODIMENTS

General Description

Figure 1:
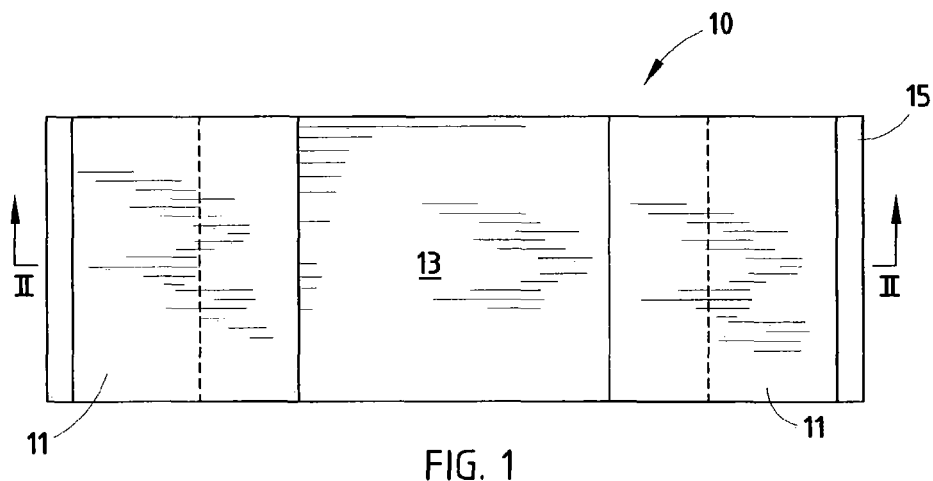
FIG. 1 is a plan view of a transdermal, dermal, transmucosal, mucosal active delivery system in accordance with a first embodiment of the present invention.

We describe herein four different embodiments of the transdermal delivery system of the present invention. The term "transdermal" as used herein is to be understood to include "transdermal," "dermal," "transmucosal" and "mucosal" delivery systems. All four embodiments share in common the handling member or members, ultra thin film, active ingredient and release liner as described above in the Summary of the Invention. The embodiments differ from one another in features such as:

variations in the nature of the "handle" or "handles" utilized in the delivery system;

other variations and configurations; and variations in the manner in which actives are carried in the system.

Although the drawings do not illustrate every possible means for carrying the active ingredient or ingredients delivered, the following are contemplated:

direct incorporation of the active ingredient(s) into the adhesive applied to the ultra thin film member;

incorporation of the active into a gel or gel pad applied to the surface of the ultra thin film (with or without a rate controlling membrane); and the use of a separate active ingredient containing "island" which itself comprises a backing member and an active ingredient containing adhesive or the like, which "island" is adhered to the adhesive coated surface of the ultra thin film.

The active ingredients used in the transdermal delivery system of the preferred embodiments are generally ingredients that are to be delivered to the patient to or through the skin or mucosa. The active ingredients may be pharmaceuticals, nutrients, perfumes, or any other ingredient that are to be delivered either topically or sub-topically on or through a patient's skin or mucosa. Exemplary pharmaceuticals include nicotine for smoking cessation programs, nitroglycerine for cardiac therapy, hormones for contraceptive use, antibiotics, and antimicrobials. With this system, the transdermal delivery system can be used to apply a drug or other ingredient dermally or mucosally while simultaneously being used to protect a wound site.

The ultra thin polymeric film used in the preferred embodiments has a thickness of less than 2 mils (0.002 inches). Preferably, its thickness is less than 1.5 mils (0.0015 inches), and typically falls within the range of from about 0.3 mils (0.0003 inches) to about 1.5 mils (0.0015 inches). The film should be very flexible, allowing it to conform readily to the user's skin or mucosa. The film must have sufficient strength to afford resistance to damage in handling and in use. It must also allow the passage of oxygen, thereby allowing the skin or mucosa to breathe. The ultra thin polymeric film material preferably is a polyurethane film. However, copolymers of polyethylene and vinyl acetate may also be used. Such ultra thin polymeric films have heretofore been used in wound dressings and I.V. hold-downs.

The advantages of using an ultra thin polymeric film backing in a transdermal or transmucosal delivery system include:

the fact that the ultra thin film creates a smaller sink, thus decreasing the extent to which the active ingredients and solubolizers used in the delivery system can migrate into the backing layer, thus mitigating the loss of effectiveness of the active ingredient due to its failure to release from the system when applied;

the ultra thin film helps to stabilize the adhesive properties of the film layers by providing a smaller sink for ingredients in the adhesive layers which might migrate into the film;

the ultra thin film material improves the breathability of the film layer or non-occlusive properties of the system;

the ultra thin film improves the flexibility and endurance of the delivery system during its use and application; and visibility and awareness of the system is reduced.

The very properties of the ultra thin film which make it desirable in use make it difficult to handle in application. The drape and flexibility properties of the ultra thin film cause it to fold over onto itself and self-adhere relatively easily, when one is trying to apply the system to the user's skin. The various different types of "handles" disclosed in the preferred embodiments obviate these shortcomings and make the delivery systems relatively easy to apply without fouling the ultra thin film material. These handles are of a stiffer and generally thicker material than that of the ultra thin film. Typical of such materials described below are plastic or paper material. Usable plastics include polyesters, polycarbonates, PVCs, polyurethanes, polyethylene vinyl acetates, polyester copolymers, polyethylenes, and polypropylenes. The paper materials may be silicon coated on the upper surface. Exemplary materials are further described below.

The various embodiments of the invention discussed below utilize various techniques for incorporating the active ingredient or ingredients into the delivery system. The methods of incorporating the active ingredient are known in the art. Examples include incorporating the active into an adhesive layer, incorporating the active into a gel layer, which may or may not employ a rate controlling membrane, or incorporating the active in liquid or solution form in some type of reservoir enclosed in a release-controlling membrane. A preferred method for incorporating the active into an adhesive or gel layer is disclosed in U.S. Pat. No. 6,576,712, which is incorporated herein by reference.

Preferred Embodiment 10

Transdermal delivery system 10 of the first embodiment comprises a pair of handling members or handles 11 attached by a layer of adhesive 12 to a rectangularly shaped, ultra thin layer of polymeric film, such as an ultra thin polyurethane film 13 (FIGS. 1 and 2), having an adhesive coated side or face and an opposite side or face that is not coated with an adhesive. The side or face of the film that is not coated with an adhesive is referred to as the non-adhesive side. A suitable thickness range for film 13 is about 0.3 mils to 1.5 mils. Handles 11 extend beyond the ends of the ultra thin polymeric film 13, as indicated by the dashed lines in FIG. 1, and as can be seen from the cross section in FIG. 2. Ultra thin polymeric film 13 is coated on its undersurface with a layer of adhesive 14, which releasably adheres to a silicone coating 16 on the top surface of release liner 15.

In preferred embodiment 10, the active ingredient is incorporated into adhesive layer 14. The techniques for doing so are known. A preferred method of incorporating the active into adhesive layer 14 is explained in U.S. Pat. No. 6,576,712, which is herein wholly incorporated by reference.

Figure 2:
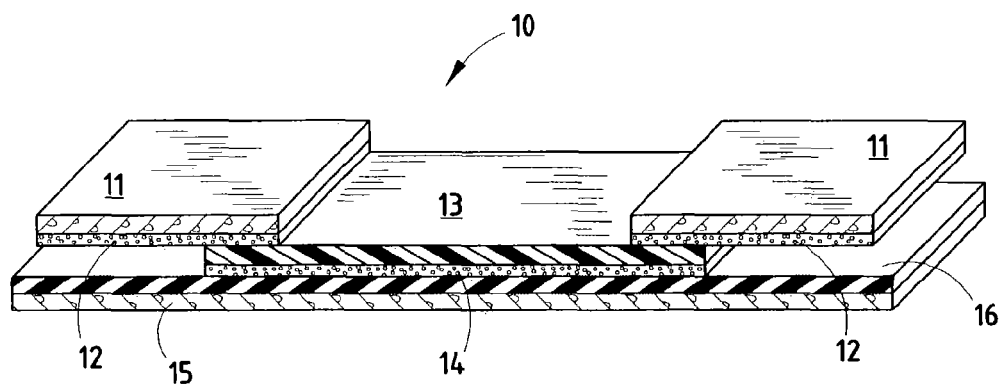
FIG. 2 is a cross sectional view of a transdermal, dermal, transmucosal, mucosal active delivery system of FIG. 1, taken along line II—II.

Handles 11 are preferably made of plastic or paper, or silicone coated paper, with the silicone coat on the upper surface thereof. Paper handles 11 are shown in FIGS. 1 and 2. The entire undersurface of each of handles 11 are coated with a pressure sensitive adhesive, which is moderately aggressive with respect to ultra thin polymeric film 13, but which does not adhere or adheres less aggressively to either the silicone coating 16 on release liner 15 or to human skin. In this way, a user can readily fold back the end portion of release liner 15 to expose the end of one of the handles 11, and the exposed handle 11 can then be used to peel film 13 away from release liner 15. The adhesive of layers 12 are "moderately aggressive" in that handles 11 remain attached to ultra thin polymeric film 13 when it is peeled away from release liner 15, and while it is being handled and applied to the patient's skin. However, pressure sensitive adhesive 12 is less aggressive with respect to its adhesion to ultra thin polymeric film 13, than is the adhesion of layer 14 on the undersurface of film 13 toward human skin or mucosa. As a result, handles 11 can be peeled away from ultra thin polymeric film 13, once film 13 is applied to the patient.

One type of adhesive which we have found useful for layers 12 on the undersurface of handles 11 is a low tack removable acrylate-based adhesives with a peel adhesive level of approximately three ounces. Other useful adhesives include, but are not limited to, silicone, urethane, synthetic rubber and natural rubber. Adhesives of this type can be formulated to have essentially no or very little adhesion to the human skin or to the silicone coating 16 on the release liner 15, but still adhere firmly but releasably to film 13.

A type of adhesive found useful for layer 14 on the undersurface of ultra thin polymeric film 13 is a permanent acrylate-based pressure sensitive adhesive designed for skin, with a peel adhesion level of approximately 50 ounces. Other useful adhesives include, but are not limited to, silicone, urethane, synthetic rubber and natural rubber. For example, one can use an acrylate derivative adhesive such as copolymers of alkyl acrylate/vinyl acetate containing —OH or/and —COOH functional groups or hydrophobic styrenic rubber polymer or PIB containing 1 to 20% hydroattractants such as PVP, PVA, and cellulose derivatives such as Duro-Tak 87-2516 (National Starch), PIB containing 20% Kollidon® CL-M (BASF). Such adhesives can be formulated to adhere releasably to the silicone coated surface 16 of the release liner 15. At the same time, they can be formulated to adhere firmly to human skin or mucosa, such that the polymeric film 13 will not peel away from the human skin or mucosa unless someone intends to do so.

Preferred Embodiment 20

Figure 3:
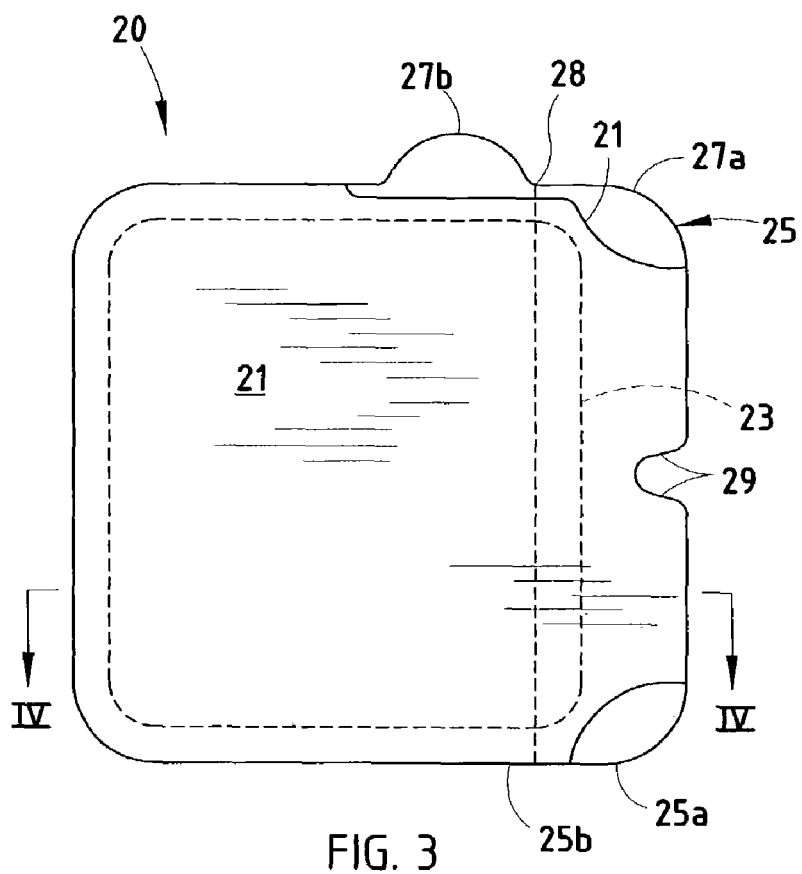
FIG. 3 is a plan view of a transdermal, dermal, transmucosal, mucosal active delivery system in accordance with a second embodiment of the present invention.
Figure 4:
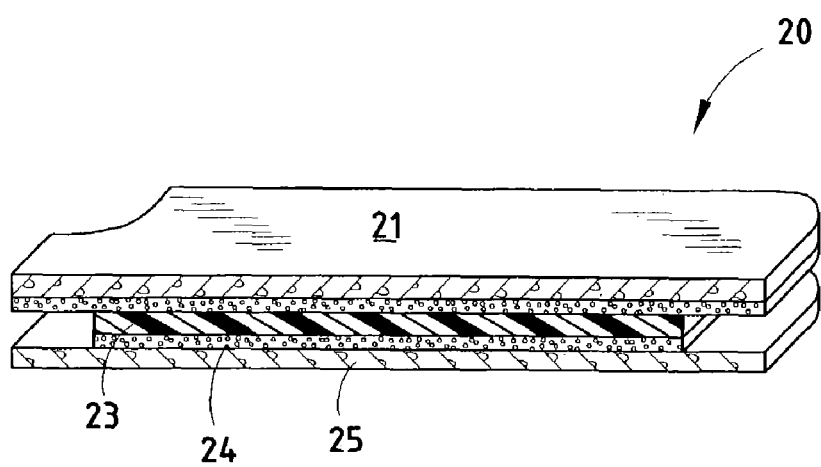
FIG. 4 is a cross sectional view of the transdermal, dermal, transmucosal, mucosal delivery system of FIG. 3, taken along line IV—IV.

Second embodiment 20 (FIGS. 3 and 4) includes handle 21, which is rectangularly shaped, extends over the entire surface of ultra thin film 23, and includes tabs 29. Handle 21 could also have a central opening, such that is covers only the portions of film 23 located towards the perimeter. Further, the release liner 25 includes tabs 27a and 27b, and is cut along line 28, forming two parts 25a and 25b. Ultra thin film 23 is coated on its underside with an active ingredient containing adhesive layer 24 (FIG. 4). Adhesively coated ultra thin polymeric film layer 23 is adhered to a release liner 25, in the same manner as ultra thin polymeric film layer 13 is adhered to release liner 15.

The purpose of providing release liner 25 in two separate sections, 25a and 25b, each having its own exposed handling tab 27a and 27b, is to facilitate ease of removal of the release liner. In use, one begins by grasping tab 27a with the thumb and forefinger of one hand, and grasping tab 27b with the thumb and forefinger of the other hand. Alternatively, one could grasp the entire assembly of release liner portion 25b, ultra thin film layer 23 and handle 21 with the thumb and forefinger of the other hand. One then peels release liner section 25a away from handle 21 and the rest of the assembly. One then grasps the handle tab 29 which is closest to release liner tab 27b with the thumb and forefinger of one hand, and grasps release liner tab 27b with the thumb and forefinger of the other hand, and peels release liner portion 25b away from the rest of the assembly. Handle 21 is then grasped by tabs 29 and used to aide in the handling of ultra thin film 23 until it is applied to a patient's skin or mucosa, at which time handle 21 is peeled away from the top surface of polymeric film 23 using tabs 29.

The active ingredient of the second embodiment 20 is incorporated into adhesive layer 24 in the same manner as the first embodiment 10.

Figure 5:
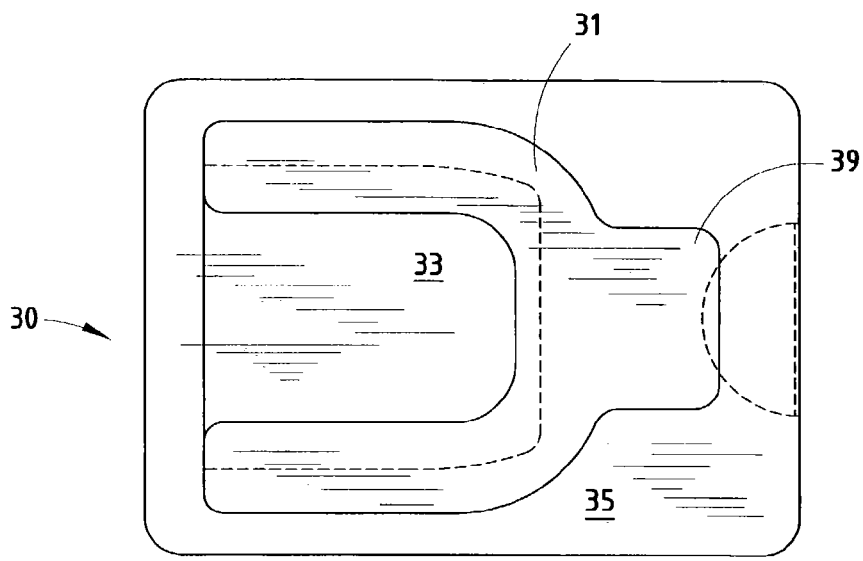
FIG. 5 is a plan view of a transdermal, dermal, transmucosal, mucosal delivery system in accordance with a third embodiment of the present invention.

Preferred Embodiment 30:

FIG. 5 discloses yet a third embodiment 30, in which the handle 31 is U-shaped, having an end tab 39 projecting from the base of the U-shape. Handling member 31 is adhered by its pressure sensitive adhesive layer to the top surface of ultra thin polymeric film layer 33 along three sides thereof, with the fourth side edge being exposed as shown in FIG. 5. This entire assembly is then applied to a silicone coated release liner 35, in the same manner as are the embodiments discussed above. In use, one folds back release liner 35 in the vicinity of tab 39, grasps tab 39 and peels the assembly of handle 31 and polymeric film 33 away from release liner 35. The applicator then applies polymeric film 33 to the patient's skin or mucosa, and then peels handle 31 away from the applied polymeric film 33.

As in embodiments 10 and 20, the active ingredient is incorporated into the adhesive layer of the ultra thin polymeric film 33.

Figure 6:
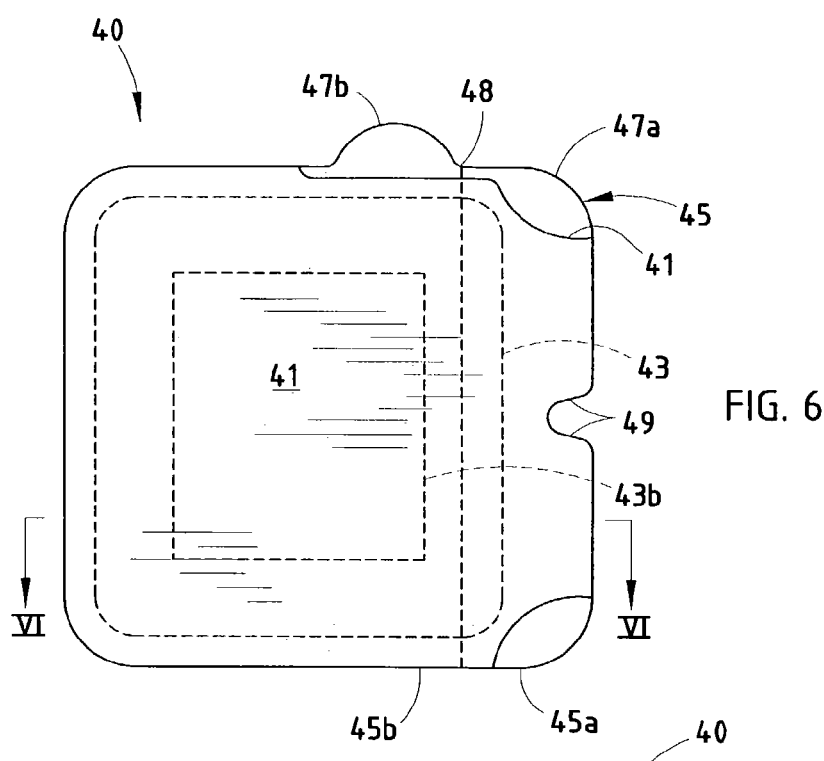
FIG. 6 is a plan view of a transdermal, dermal, transmucosal, mucosal active delivery system in accordance with a fourth embodiment of the present invention.
Figure 7:
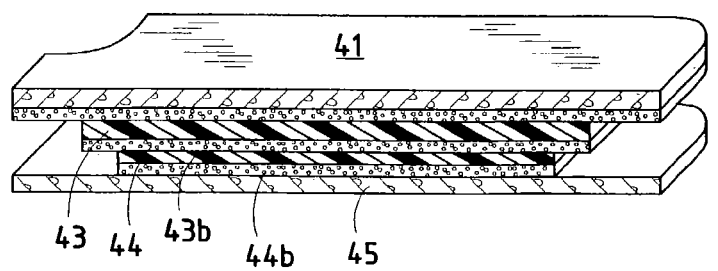
FIG. 7 is a cross sectional view of the transdermal, dermal, transmucosal, mucosal delivery system of FIG. 6, taken along line VI—VI.

Preferred Embodiment 40:

FIGS. 6, and 7 disclose a fourth embodiment 40, in which the handle 41 is the same as the second embodiment discussed above, extending over the entire surface of ultra thin film 43, and includes tabs 49. Handle 41 may also have a central opening, such that it covers only the portions of film 43 located towards the perimeter. Further, the release liner 45 includes tabs 47a and 47b, and is cut, forming two parts 45a and 45b, along cut line 48. Ultra thin film 43 is coated on its underside with an adhesive layer 44 (FIG. 4). However, in this embodiment adhesive layer 44 does not contain an active ingredient. Film 43 is concentrically positioned over, adhered to by adhesive layer 44, and overhangs an active ingredient containing "island."

The active ingredient containing island comprises a backing member 43b which may be an ultra thin polymeric film, a thicker polymeric film, a metallized polymeric material, or other film like backing material. Using a metal or metallized film helps minimize migration of ingredients from the active ingredient island into ultra thin film layer 43. However, in some applications, especially where active ingredient containing layer 44b, adhered to backing member 43b, has to be fairly large, it is preferable to use a breathable polymeric film as backing member 43b. Preferably, it should also be waterproof.

The assembled handle 41, ultra thin film 43 and active ingredient island 43b, 44b are adhered to release liner 45 in the same manner as ultra thin polymeric film layer 23 is adhered to release liner 25 in the second embodiment. In use, one removes the release liner and applies delivery system 40 as in second embodiment 20.

Active ingredient containing layer 44b can comprise any of the various drug delivery configurations used in transdermal/dermal/transmucosal/mucosal delivery systems. Thus, it can be an active ingredient containing adhesive layer. Alternatively, it can comprise an active ingredient containing gel layer, or a membrane mediated active ingredient containing gel layer. In a membrane mediated system, the active ingredient can be in liquid form, as for example contained in a solution, where the rate mediated membrane comprises or is part of a pouch containing the liquid. Backing member 43b may include an adhesive layer to which gel layer or membrane pouch is adhered. As above, the preferred method for incorporating the active into an adhesive or gel layer is disclosed in U.S. Pat. No. 6,576,712, issued Jun. 10, 2003.

It will be appreciated by those skilled in this art that there are a number of different ways in which the various embodiments of the invention can be manufactured. What is common to all, is that the present invention makes it possible to apply pressure sensitive adhesive to the entire undersurface of the handles (11, 21, 31, or 41) of the products, and press the handles onto the non-adhesive side of the ultra thin polymeric film (13, 23, 33, or 43) with adhesive coated portions of the handles extending beyond (overhanging) the edges of the film, and press the release liner (15, 25, 35 or 45) onto the adhesive side of the film, with the release liner extending beyond the edges of the film to the same extent as the handles, to a lesser extent, or further if desired.

The foregoing are preferred embodiments of the invention and changes and variations can be made without departing from the spirit and broader aspects of the invention, as defined in the appended claims, which are to be interpreted in accordance with the principles of patent law, including the Doctrine of Equivalents.

The invention claimed is:

1. A transdermal, transmucosal active delivery system comprising:
   an ultra thin polymeric film member having a thickness of less than 0.002 inches;
   a layer of adhesive coating at least a portion of a first side of said ultra thin film, whereby said layer of ultra thin film can be adhered to a dermal or mucosal layer;
   a transdermally-effective active ingredient secured to said first side of said ultra thin film, wherein said transdermally-effective active ingredient is contained in an island member whose dimension are less extensive in scope then the dimensions of said ultra thin film, said island member comprising a backing member to which said transdermally-effective active ingredient is secured, said backing member being adhered to said ultra thin film layer by said first adhesive layer; and wherein said transdermally-effective active ingredient is incorporated into a layer of adhesive which is applied to said island backing member.

2. A transdermal-dermal, transmucosal-mucosal delivery system comprising:
   a handle having a first adhesive coated on a first side thereof;
   an ultra thin polymeric film with a thickness under 0.002 inches and having a first and a second side;
   a second adhesive layer on the first side of said ultra thin film, the first adhesive of the handle being adhered to the second side of said ultra thin film, said handle at least partially extending beyond at least one edge of the said ultra thin film;
   a transdermally-effective pharmacologically active ingredient secured to said first side of said ultra thin film;
   a release liner adhered to and covering said first side of said ultra thin film, including said second adhesive layer and said transdermally-effective active ingredient, said liner at least partially extending beyond at least one edge of said ultra thin film such that it also at least partially covers said first adhesive layer on said handle;
   wherein the second adhesive adheres more aggressively to skin or mucosa than said first adhesive adheres to said second side of said ultra thin film, whereby said handle can be removed from the second side of the ultra thin film once the first side of said ultra thin film is adhered to a patient's skin or mucosa, and wherein said first side of said handle is entirely coated with the first adhesive, said first adhesive comprises a pressure sensitive adhesive which does not adhere to said release liner, or to skin, or mucosa.

3. A transdermal-dermal, transmucosal-mucosal delivery system comprising:
   a handle having a first adhesive coated on a first side thereof;
   an ultra thin polymeric film with a thickness under 0.002 inches and having a first and a second side;
   a second adhesive layer on the first side of said ultra thin film, the first adhesive of the handle being adhered to the second side of said ultra thin film, said handle at least partially extending beyond at least one edge of the said ultra thin film;
   a transdermally-effective pharmacologically active ingredient secured to said first side of said ultra thin film;
   a release liner adhered to and covering said first side of said ultra thin film, including said second adhesive layer and said transdermally-effective active ingredient, said liner at least partially extending beyond at least one edge of said ultra thin film such that it also at least partially covers said first adhesive layer on said handle;
   wherein the second adhesive adheres more aggressively to skin or mucosa than said first adhesive adheres to said second side of said ultra thin film, whereby said handle can be removed from the second side of the ultra thin film once the first side of said ultra thin film is adhered to a patient's skin or mucosa; and wherein said first adhesive comprises a pressure sensitive adhesive which does not adhere to said release liner, or to skin, or mucosa.

4. A transdermal-dermal, transmucosal-mucosal delivery system comprising:
   a handle having a first adhesive coated on a first side thereof;
   an ultra thin polymeric film with a thickness of less than 0.002 inches and having a first and a second side;
   a second adhesive coated on the first side of said ultra thin film, the first adhesive of the handle being adhered to the second side of said ultra thin film, said handle at least partially extending beyond at least one edge of the said ultra thin film;

a transdermally-effective active ingredient contained in an island member whose dimensions are less extensive in scope than the dimensions of said ultra thin film, said island member comprising a backing member to which said active ingredient is secured, said backing member being adhered to said ultra thin film layer by said second adhesive layer;

a release liner adhered to and covering said first side of said ultra thin film, including said second adhesive layer and said transdermally-effective active ingredient, said liner at least partially extending beyond at least one edge of said ultra thin film such that it also at least partially covers said first adhesive layer on said handle;

wherein the second adhesive adheres more aggressively to skin or mucosa than said first adhesive adheres to said second side of said ultra thin film, whereby said handle can be removed from the second side of the ultra thin film once the first side of said ultra thin film is adhered to a patient's skin or mucosa; and wherein said transdermally-effective active ingredient is incorporated into a layer of adhesive which is applied to said island backing member.

5. A transdermal-dermal, transmucosal-mucosal delivery system comprising:

a handle having a first adhesive coated on a first side thereof;

an ultra thin polymeric film with a thickness of less than 0.002 inches and having a first and a second side;

a second adhesive coated on the first side of said ultra thin film, the first adhesive of the handle being adhered to the second side of said ultra thin film, said handle at least partially extending beyond at least one edge of the said ultra thin film;

a transdermally-effective active ingredient contained in an island member whose dimensions are less extensive in scope than the dimensions of said ultra thin film, said island member comprising a backing member to which said active ingredient is secured, said backing member being adhered to said ultra thin film layer by said second adhesive layer;

a release liner adhered to and covering said first side of said ultra thin film, including said second adhesive layer and said transdermally-effective active ingredient, said liner at least partially extending beyond at least one edge of said ultra thin film such that it also at least partially covers said first adhesive layer on said handle;

wherein the second adhesive adheres more aggressively to skin or mucosa than said first adhesive adheres to said second side of said ultra thin film, whereby said handle can be removed from the second side of the ultra thin film once the first side of said ultra thin film is adhered to a patient's skin or mucosa; and wherein said transdermally-effective active ingredient is incorporated into a gel layer adhered to said island backing member, and said transdermally-effective active ingredient is incorporated into a layer of adhesive which is applied to said island backing member.

6. A transdermal-dermal, transmucosal-mucosal delivery system comprising:

a handle having a first adhesive coated on a first side thereof;

an ultra thin polymeric film with a thickness of less than 0.002 inches and having a first and a second side;

a second adhesive coated on the first side of said ultra thin film, the first adhesive of the handle being adhered to the second side of said ultra thin film, said handle at least partially extending beyond at least one edge of the said ultra thin film;

a transdermally-effective active ingredient contained in an island member whose dimensions are less extensive in scope than the dimensions of said ultra thin film, said island member comprising a backing member to which said active ingredient is secured, said backing member being adhered to said ultra thin film layer by said second adhesive layer;

a release liner adhered to and covering said first side of said ultra thin film, including said second adhesive layer and said transdermally-effective active ingredient, said liner at least partially extending beyond at least one edge of said ultra thin film such that it also at least partially covers said first adhesive layer on said handle;

wherein the second adhesive adheres more aggressively to skin or mucosa than said first adhesive adheres to said second side of said ultra thin film, whereby said handle can be removed from the second side of the ultra thin film once the first side of said ultra thin film is adhered to a patient's skin or mucosa; and wherein said transdermally-effective active ingredient is incorporated into a layer of adhesive which is applied to said island backing member, and said transdermally-effective active ingredient is contained in a reservoir adhered to said island backing member.

7. A transdermal-dermal, transmucosal-mucosal delivery system comprising:

a handle having a first adhesive coated on a first side thereof;

an ultra thin polymeric film with a thickness of less than 0.002 inches and having a first and a second side;

a second adhesive coated on the first side of said ultra thin film, the first adhesive of the handle being adhered to the second side of said ultra thin film, said handle at least partially extending beyond at least one edge of the said ultra thin film;

a transdermally-effective active ingredient contained in an island member whose dimensions are less extensive in scope than the dimensions of said ultra thin film, said island member comprising a backing member to which said active ingredient is secured, said backing member being adhered to said ultra thin film layer by said second adhesive layer;

a release liner adhered to and covering said first side of said ultra thin film, including said second adhesive layer and said transdermally-effective active ingredient, said liner at least partially extending beyond at least one edge of said ultra thin film such that it also at least partially covers said first adhesive layer on said handle;

wherein the second adhesive adheres more aggressively to skin or mucosa than said first adhesive adheres to said second side of said ultra thin film, whereby said handle can be removed from the second side of the ultra thin film once the first side of said ultra thin film is adhered to a patient's skin or mucosa; and wherein said first adhesive comprises a pressure sensitive adhesive which does not adhere to said release liner, or to skin, or mucosa.

* * * * *